United States Patent [19]
Larison, II

[11] Patent Number: 6,088,609
[45] Date of Patent: Jul. 11, 2000

[54] APPARATUS AND METHOD FOR MONITORING A FETUS

[76] Inventor: Wayne A. Larison, II, 12335 S. Locust Cir., Olathe, Kans. 66062

[21] Appl. No.: 09/108,023

[22] Filed: Jun. 30, 1998

[51] Int. Cl.[7] ................................................. A61B 5/0448
[52] U.S. Cl. ........................................... 600/376; 439/909
[58] Field of Search ...................... 600/376, 511, 600/338, 351; 607/127, 131; 439/909

[56] References Cited

U.S. PATENT DOCUMENTS

| | | |
|---|---|---|
| 3,120,227 | 2/1964 | Hunter, Jr. et al. . |
| 4,157,710 | 6/1979 | Abitbol . |
| 4,873,986 | 10/1989 | Wallace . |
| 5,199,432 | 4/1993 | Quedens et al. ........................ 600/376 |
| 5,205,288 | 4/1993 | Quedens et al. ........................ 600/376 |
| 5,425,362 | 6/1995 | Siker et al. . |
| 5,615,674 | 4/1997 | Maurer ................................... 600/376 |
| 5,680,859 | 10/1997 | Urion et al. ............................. 600/376 |

*Primary Examiner*—Lee S. Cohen
*Attorney, Agent, or Firm*—Kenneth L Tolar

[57] ABSTRACT

A fetal monitoring assembly includes an electrode housing having a top and bottom end with a spiraled electrode extending from the top end thereof. Extending from the bottom end is flat plate and a plurality of wires which couple the electrode with a fetal monitor. The wires are encompassed within an elongated tube having first and second ends with a pair of opposing notches at a first end dimensioned to receive the electrode plate. The tube is formed of two mating semi-cylindrical sections which may be separated when removing the tube. The terminal end of each wire has a female electrical receptacle for conveniently coupling the wires to a fetal video monitor plug. A second end of the tube has a circumferential removable strip which compresses the tube about the wires and prevents the two sections from separating until the user has properly installed the electrode.

6 Claims, 2 Drawing Sheets

APPARATUS AND METHOD FOR MONITORING A FETUS

BACKGROUND OF THE INVENTION

The present invention relates to a disposable electrode assembly which may be quickly and conveniently connected to a fetal monitor and discarded after use.

DESCRIPTION OF THE PRIOR ART

Fetal monitoring devices are used by health care workers to carefully monitor the heartbeat of a fetus immediately prior to childbirth. A conventional assembly relates to an electrode secured to an end of a housing tube with the electrode wiring received therein. A second hollow tube is normally used as a guide tube when attaching the electrode to the fetus. The tube has a releasable gripping device at an opposing end to secure the wires therewith when maneuvering the electrode. Because the tube is removed from the wires after the electrode is attached, the terminal ends of the electrode wires are usually stripped and exposed since electrical connectors would require the tube to be cut to release the wires. Accordingly, when connecting the electrode wire to the fetal monitor, the stripped wire leads are typically wrapped about a plug type connector. The resulting connection is tenuous and may be easily separated with minimal impact or movement. Accordingly, there is currently a need for a device which allows a fetal monitor electrode to be securely attached to a fetal monitor cord while allowing the tube to be simultaneously separated from the wires.

Various fetal monitoring devices exist in the prior art. For example, U.S. Pat. No. 3,120,227 issued to Hunter generally discloses a method for obtaining a fetal electrocardiogram using a novel scalp probe that delivers a signal to various electronic translation and recording equipment. The method also includes selective placement of the electrodes on the mother's body so that her heart signals do not interfere with that of the baby.

U.S. Pat. No. 4,157,710 issued to Abitbol discloses an abdominal electrode for fetal monitoring having a spiraled tip that is inserted through the wall of the mother's stomach so that the baby's heart can be monitored. The electrode is attached to a handle inside of which is a female connector engaging a corresponding male connector and wire that carries the signal to monitoring equipment.

U.S. Pat. No. 4,873,986 issued to Wallace describes an apparatus for monitoring intrauterine pressure and fetal heart rate comprising a transducer apparatus at one end of a cable and a plug type device at the other. The transducer end is inserted into the uterus to monitor pressure therein as well as the fetus' heart rate.

U.S. Pat. No. 5,425,362 issued to Siker discloses a fetal sensor device comprising a housing with numerous sensors therein. The housing has a flexible distal end and fits about the fetus in utero.

Although various fetal monitoring devices exist in the prior art, none relate to an assembly according to the present invention including an electrode wired to a pair of plug type receptacles which may be quickly coupled with a fetal monitor. Furthermore, the device comprises a guide tube surrounding the electrode wire formed of two mating semi-cylindrical sections allowing the two sections to be conveniently separated from the wires once the device is secured to a fetus' skin.

SUMMARY OF THE INVENTION

The present invention relates to a fetal monitor assembly including an electrode housing having a spiraled electrode at an end thereof. Extending from the opposing end of the electrode housing are a plurality of wires for electrically connecting the electrode to a video monitor. The wires are surrounded by an elongated tube having a pair of opposing notches at a first end thereof. The notches receive a plate secured to the bottom end of the electrode housing to assist in maneuvering the electrode during the installation process. The tube is formed of two mating semi-cylindrical sections each having a pair of opposing terminal edges. Each terminal edge of a first semi-cylindrical section has an inwardly depending flange. Each terminal edge of the opposing semi-cylindrical section has a substantially V-shaped portion for receiving the flange on the opposing semi-cylindrical section allowing the tube to be separated from the electrode wires once the electrode is installed. At the second end of the tube is a removable, circumferential strip which tightly compresses the tube against the wires to hold the electrode plate within its notches. A female electrical receptacle is attached to the terminal end of each wire and is dimensioned to receive a male plug on a Y-type electrical connector found on conventional fetal video monitor cords. Accordingly, once the electrode is installed, the wires may be quickly and conveniently attached to a video monitor cord providing a secure connection. The strip is removed and the tube is gradually retracted and separated from the electrode wires without disturbing or interrupting the electrical connection. It is therefore an object of the present invention to provide a fetal monitoring assembly which may be quickly and securely coupled with a fetal monitoring device.

It is yet another object of the present invention to provide a fetal monitoring assembly that includes a separable guide tube allowing the tube to be conveniently removed once installed.

It is yet another object of the present invention to provide a fetal monitoring assembly that prevents the electrode wiring from being detached from the fetal monitor. Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
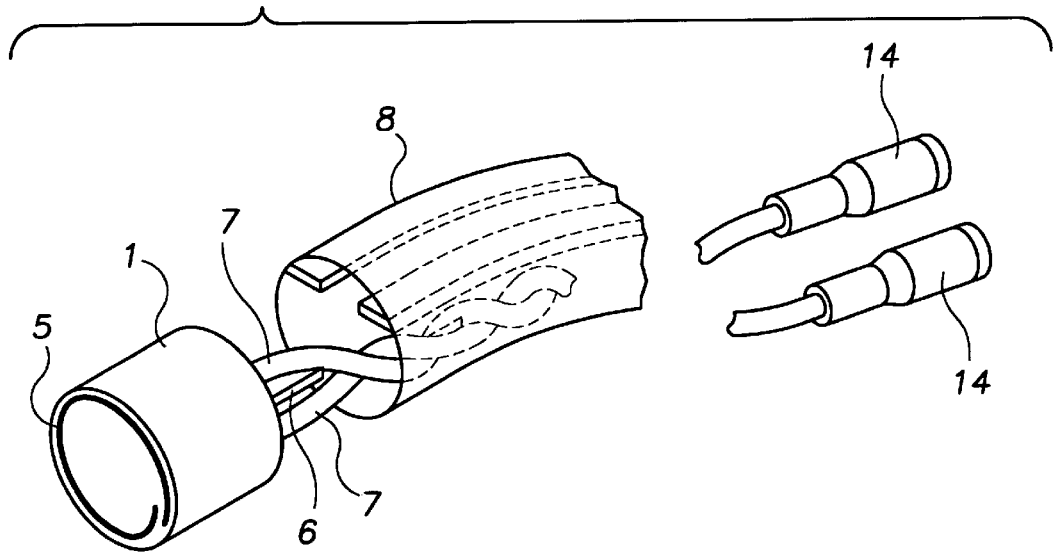
FIG. 1 depicts the electrode secured to a first end of the separable tube with the terminal ends of the wires adjacent thereto.
Figure 2:
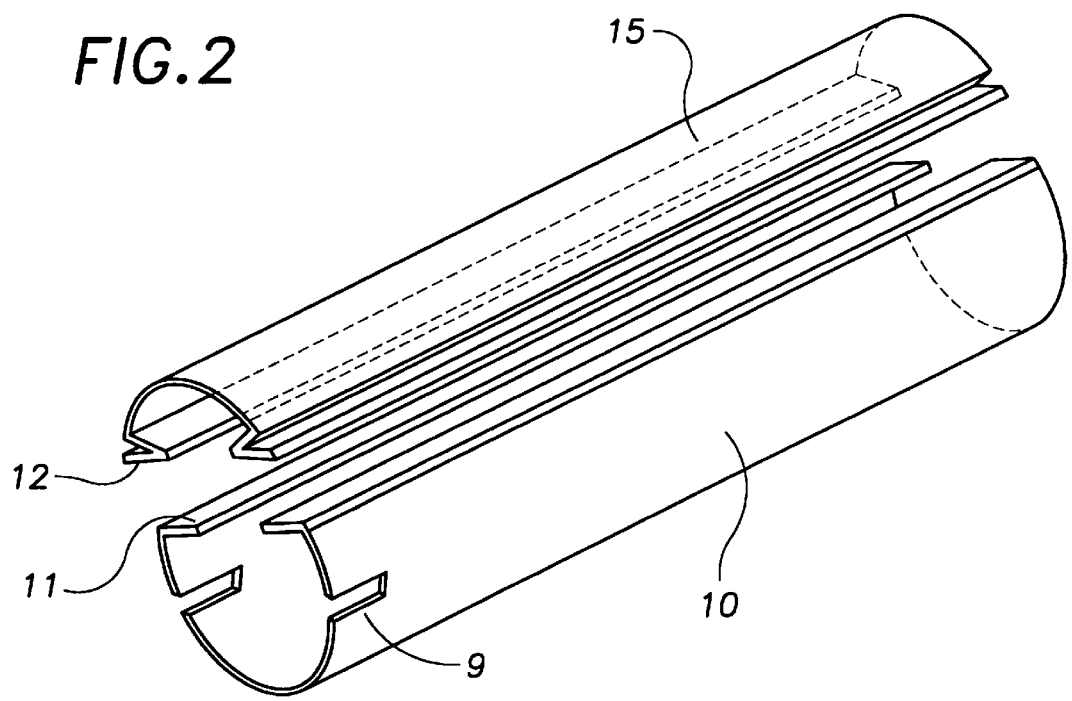
FIG. 2 depicts the separable tube.
Figure 3:
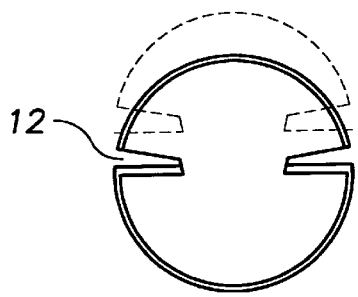
FIG. 3 is an end view of the separable tube.
Figure 4:
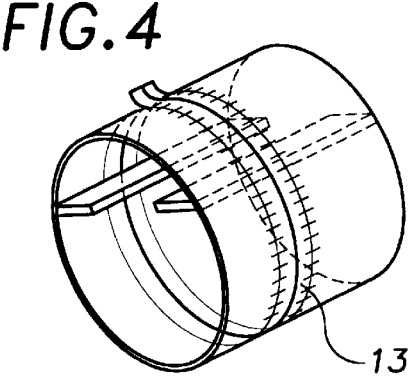
FIG. 4 depicts the pull tab mechanism according to the present invention.
Figure 5:
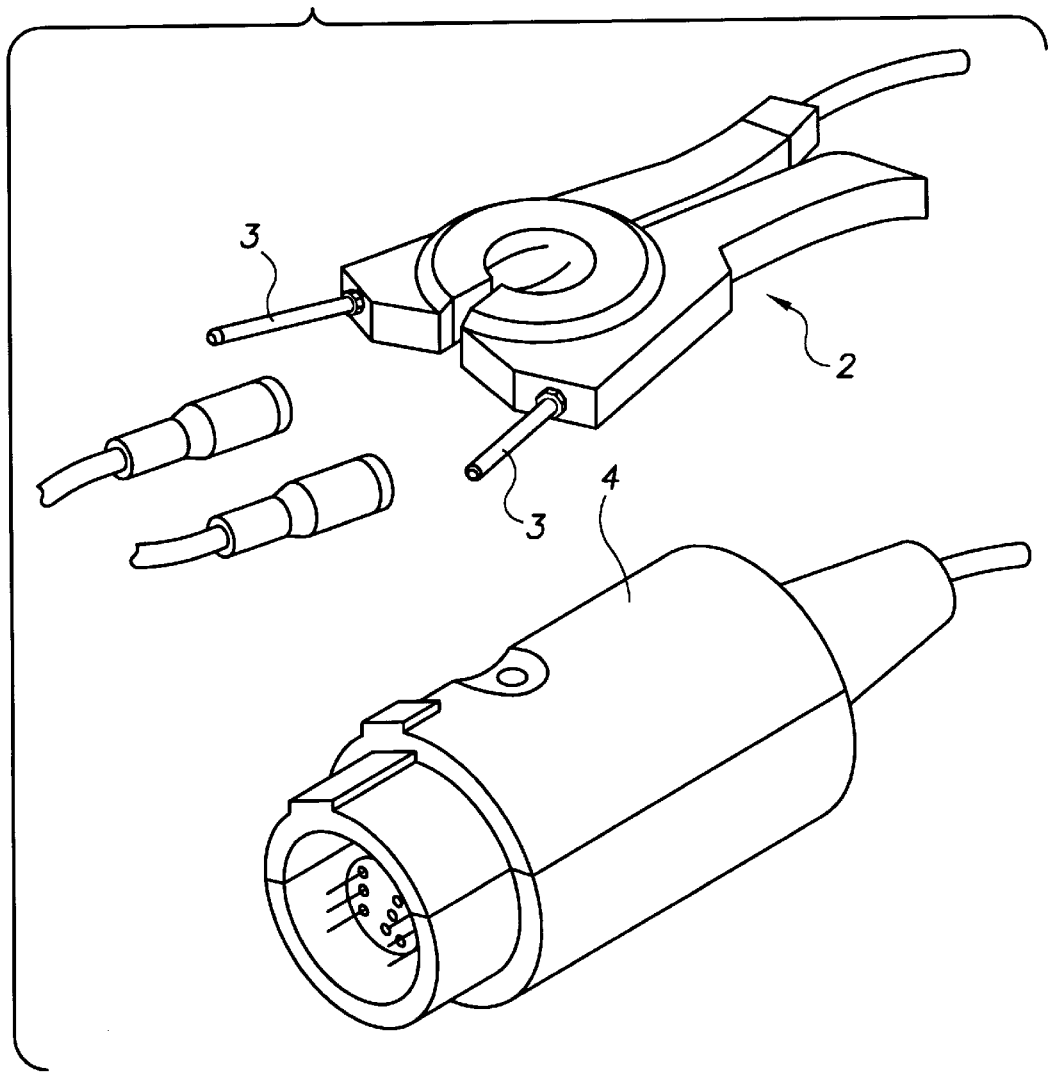
FIG. 5 depicts the electrode wires adjacent the conventional fetal monitor plug assembly.

Referring now to FIGS. 1 through 5, the present invention relates to a fetal monitor electrode assembly which may be conveniently coupled with a fetal monitor. A conventional fetal monitor typically includes a video monitor having a socket thereon for receiving a plug member 4 on a cord. The opposing end of the cord has a Y-type connector 2 with a pair of diverging male electrical prongs 3 extending therefrom. The present invention provides an assembly for coupling a fetal monitor electrode with a Y-type connector as described above.

The device comprises an electrode housing 1 having a top and bottom end with a spiraled electrode 5 extending from the top end thereof. Extending from the bottom end is a substantially flat plate 6 and a pair of electrode wires 7 which are in communication with the spiraled electrode.

Surrounding the wires is an elongated preferably transparent guide tube 8 having first and second ends. At a first end of the tube are a pair of opposing notches 9 for receiving the flat plate on the electrode housing. The notches allow the tube to maneuver the electrode during the installation process. The tube is formed of two mating separable semi-cylindrical portions. Each semi-cylindrical portion has a pair of terminal edges which mate with the terminal edges of the opposing section. A first section 10 has an inwardly depending flange 11 at each terminal edge. The opposing section 15 has a V-shaped portion 12 at each terminal edge for slidably receiving the flange on the opposing section.

The second end of the tube has a circumferential strip 13 that compresses the tube against the wires to retain the plate within its corresponding notches during the insertion process. The strip may be secured to the tube with a series of perforations and may have an adhesive on a side thereof for adhesively securing to the wires. In either case, once the electrode is properly installed, the pull tab is removed to release the wires allowing the tube to be separated and discarded while the electrode remains in place.

The terminal ends of the wires each have a female type electrical receptacle 14 attached thereto dimensioned to tightly receive the male connectors on the conventional Y-type connector. The receptacles provide a secure and convenient electrical connection that will not detach when bumped or moved.

To use the above described assembly, the electrode and the attached removable sleeve may be inserted into a mother until the electrode is in its desired position. The female receptacles at the terminal ends of the electrode wires may be quickly and securely coupled to the fetal monitor Y-connector. The circumferential strip is then separated from the tube allowing the tube to be retracted independent of the wires. The electrode remains attached to the fetus during the delivery process after which time the entire assembly may be discarded. As detailed above, the present invention provides a unique fetal electrode assembly that provides plug type connectors at the terminal ends of the electrode wires while allowing the guide tube to be separated therefrom.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A fetal monitoring assembly comprising:
   an electrode housing having a top and bottom end with an electrode at the top end and a flat plate extending from the bottom end;
   a plurality of wires electrically connected to said electrode and protruding from the bottom end of the electrode housing, each of said wires having a terminal end;
   an electrical receptacle secured to each terminal end of said wire, said receptacle configured to receive a male electrical prong on a fetal video monitor cord to quickly and securely establish communication between the electrode and a video monitor;
   an elongated tube surrounding said wires, said tube having first and second ends with a pair of opposing notches at a first end for receiving the flat plate on the bottom end of said electrode housing to facilitate the maneuvering of said electrode into the womb of a mother; said tube further including two separable sections for separating said tube from said wires once said electrode is properly secured to a fetus, said tube sections including a pair of terminal edges, a first one of said sections having an inwardly depending flange at each terminal edge thereof, the other section having a substantially V-shaped portion at each edge thereof for slidably receiving the flange on said first section allowing each of said sections to be separated to release the electrode wires therefrom.

2. A device according to claim 1 wherein said tube further comprises a circumferential strip proximal the second end for compressing said tube against said wires, said strip being removable from said tube for releasing said wires from said tube.

3. A device according to claim 2 wherein said strip is removably secured to said tube with perforations.

4. A device according to claim 2 wherein said strip has an adhesive on a side thereof for removably attaching said strip about the exterior of said wires.

5. A fetal monitoring assembly comprising:
   an electrode housing having a top and bottom end with an electrode at the top end and a flat plate extending from the bottom end;
   a plurality of wires electrically connected to said electrode and protruding from the bottom end of the electrode housing, each of said wires having a terminal end;
   an electrical receptacle secured to each terminal end of said wire, said receptacle configured to receive a male electrical prong on a fetal video monitor cord to quickly and securely establish communication between the electrode and a video monitor;
   an elongated tube surrounding said wires, said tube having first and second ends with a pair of opposing notches at a first end for receiving the flat plate on the bottom end of said electrode housing to facilitate the maneuvering of said electrode into the womb of a mother; said tube further including two separable sections for separating said tube from said wires once said electrode is properly secured to a fetus;
   a circumferential strip proximal the second end of said tube for compressing said tube against said wires, said strip being removable from said tube for releasing said wires from said tube.

6. A method for connecting a fetal monitor electrode to a fetal monitor comprising the steps of:
   placing a separable tube about a plurality of wires, the first ends of which are connected to a fetal monitor electrode;
   connecting a female receptacle to the opposing end of each of said wires;
   inserting said electrode into the womb of a mother and securing said electrode to a fetus;
   coupling each of said receptacles with a male electrical connector on a conventional fetal video monitor cord;
   placing a removable strip about an end of said tube to compress the tube about said wires when inserting said electrode into the womb of a mother;
   removing said strip;
   separating and discarding said tube when said electrode is secured to a fetus.

* * * * *